United States Patent [19]

Fussi

[11] 4,391,803
[45] Jul. 5, 1983

[54] ADRENOSTERIOD COMPOSITION AND METHOD FOR THE TREATMENT OF SHOCK BY INFUSIONAL THERAPY

[75] Inventor: Fernando F. Fussi, Fribourg, Switzerland

[73] Assignee: Hepar Industries, Franklin, Ohio

[21] Appl. No.: 375,749

[22] Filed: May 6, 1982

Related U.S. Application Data

[63] Continuation-in-part of Ser. No. 365,867, Apr. 5, 1982, abandoned.

[51] Int. Cl.³ .............................................. A61K 31/56
[52] U.S. Cl. ..................................................... 424/239
[58] Field of Search ........................................ 424/239

[56] References Cited

PUBLICATIONS

Chemical Abstracts, vol. 80, (1974), Par. 78,634(f).

Primary Examiner—Elbert L. Roberts
Attorney, Agent, or Firm—Cushman, Darby & Cushman

[57] ABSTRACT

Septic shock and other forms of shock are effectively treated using a blend of 18 different adrenosteroids in their physiologic ratios based upon an animal cortex extract as a model. The blend preferably administered by infusion to a person suffering from shock. The blend is more effect and at a lower dosage level than hydrocortisone base or water-soluble derivatives of hydrocortisone.

11 Claims, No Drawings

ADRENOSTERIOD COMPOSITION AND METHOD FOR THE TREATMENT OF SHOCK BY INFUSIONAL THERAPY

CROSS-REFERENCE TO RELATED APPLICATIONS

This application is a continuation-in-part of my earlier application Ser. No. 365,867, filed Apr. 5, 1982, and now abandoned.

BACKGROUND OF THE INVENTION

Hydrocortisone and semi-synthetic analogs, such as methyl prednisolone and dexamethasone, have been extensively used in prevention and therapy of different forms of shock, as for instance: (a) septic shock and subsequent abdominal infarction, at a dose of 25-30 mg/Kg, W. Schumer, Ann. Surg. 184,333 (1976), or acute peritonitis (post-operative or from appendicitis, perforated gastrointestinal ulcer, intestinal occlusion, enteritis, neoplastic perforation of colon and other causes) complicated by endotoxin shock, P. Stefanini, V. Speranza, Postgrad. Med. J. 43,79 (1967); (b) shock from burns at a booster dose of 2-3 gr. of hydrocorisone or equivalent doses of other semi-synthetic steroids, M. O. Chiaradia, B. Gagliardi, G. C. Serra, Arch. Osp. Mare 20,432 (1968); and (c) traumatic shock, at 50 mg/Kg associated with low molecular weight dextran (LMWD) at 2 gr/Kg, G. C. Serra, M. Simone, Acta Anesthes. 16, suppl., 195 (1965).

The actions of hydrocortisone in shock, specifically endotoxin-shock, can be summarized as follows: blockage of adrenergic receptors; "permissive" action, i.e., normalization of the effects of catecholamines on arteriolocapillary bed; increase of capillary resistance; and endotoxin-specific antitoxic activity.

Glucocorticoid therapy in shock prevention and therapy must be associated with other therapeutic agents, such as plasma volume expanders (dextrans), antibiotics, Aprotinin (protease inhibitor), alpha-adrenergic blocking agents (phenoxybenzamine) or, as an alternative, pressor agents (Levarterenol or Metaraminol). In shock therapy the recommended dosage for hydrocortisone is at least 300 mg; see Goodman and Gilman, "The Pharmacological Basis of Therapeutics" 5th Ed., pg. 1501 (1975). Due to the very low solubility in water of the bases—as an example at 25° C., only 280 mg hydrocortisone base dissolves in 1000 ml water—hydrocortisone and methylprednisolone hydrosoluble derivatives, typically sodium hemisuccinates or sodium phosphates, must be administered by injection. Unfortunately, these derivatives are less active than the bases, and consequently larger amounts must be administered, i.e., up to 2-10 gr, to achieve a therapeutic effect. The administration of such a large amount of one single steroid impairs the physiological hormonal equilibrium and produces unwanted side effects.

DETAILED DESCRIPTION OF THE INVENTION

In my studies I have made discoveries about corticoid administration and have found that a composition containing a blend of all the corticosteroids (as bases), including metabolites present in an adrenal cortex extract in their physiological ratios, shows a higher pharmacological activity than hydrocortisone base alone. In some experimental models, as further described below, this composition (hereafter referred to for convenience as "adrenosteroids") exhibits a potency that is about 3:1 compared with hydrocortisone base and about 20:1 compared with hydrocortisone hemisuccinate.

Due to the lower dosage needed for use and to be physiologically balanced, the adrenosteroids formulation of my invention causes very low or no side effects and the therapy can be safely prolonged.

The adrenosteroids formulation of my invention ameliorates the drop in blood pressure; this is of paramount importance in shock therapy. By contrast hydrocortisone by itself has no effect on blood pressure. For this reason, one of the biggest problems in shock management is the decision to also utilize alpha-blockers that further lower the blood pressure, or pressor agents as an alternative.

A solution of 600 mcg/ml of the novel adrenosteroids formulation herein disclosed in water is perfectly stable, if prepared according to the procedures set forth in detail below: compare with hydrocortisone base solubility, not more than 250 mcg/ml. Therefore, 250 and 500 ml containers for infusion, each containing, respectively, 150 and 300 mg adrenosteroids in a suitable vehicle or carrier such as isotonic saline solution, human plasma, protein hydrolysate injection, glucose, or in dextran solutions, can be safely prepared and stored. The adrenosteroids formulations of my invention may also be used as replacers of cortisone administration in immunosoppressive therapy and in treatment of malignancies. In fact, the side effects of cortisone therapy are well known and can be overcome by adrenosteroid administration. Other uses and applications will be apparent to the skilled clinician.

Inclusion of adrenocorticoids in parenteral nutrients, i.e., fat emulsion could potentially increase the concentration of adrenocorticoids in a finished form.

Adrenosteroids Assay: Chemical assays and quanlitative test necessary to identify and quantify the ingredients of the compositions are made according to methods that are well known in the art. Total steroids are extracted from an aqueous solution by chloroform and determined by tetrazolium blue (BTZ) reaction against a hydrocortisone standard solution at 525 nm. Steroids are singly separated in the chloroform extract by bi-dimensional thin layer chromatography (TLC). The developers used are UV, BTZ, p-Anysaldehyde and Isoniazide. Also liquid-liquid chromatography (LLC) can be used with a suitable detector.

The adrenosteroid compositions of my invention contain the following components:

TABLE I

| | Compound | Trade Name | /(Merck)* Abbrev. | Percentage** |
|---|---|---|---|---|
| 1. | 11-Dehydrocorticosterone | Kendall A | A (2844) | 10.0 ± 1.5 |
| 2. | Corticosterone | Kendall B | B (2513) | 18.5 ± 2.5 |
| 3. | 11-Deoxy-17-hydroxy-corticosterone | Reichstein S | S (2891) | 3.0 ± 0.5 |
| 4. | Cortisone | Kendall E | E (2514) | 14.0 ± 2.0 |

TABLE I-continued

| | Compound | Trade Name | Abbrev. /(Merck)* | Percentage** |
|---|---|---|---|---|
| 5. | Hydrocortisone | Kendall F | F (4674) | 23.0 ± 3.5 |
| 6. | 4-Pregnene-20,21-diol-3,11-dione | Reichstein T | DHA (7529) | 2.0 ± 0.5 |
| 7. | 4-Pregnene-17α,20β,21-triol-3,11-dione | Reichstein U | DHE (7531) | 2.0 ± 0.5 |
| 8. | 4-Pregnene-11β,17α,20β,21-tetrol-3-one | Reichstein E | DHF (7530) | 3.0 ± 0.5 |
| 9. | Allopregnane-3α or 3β,21-diol-11,20-dione | Reichstein N | THA (255) | 2.5 ± 0.5 |
| 10. | Allopregnane-3α or 3β,11β,21-triol-20-one | Reichstein R | THB (265) | 3.0 ± 0.5 |
| 11. | Allopregnane-3α or 3β,17α,21-triol-20-one | Reichstein P | THS (266) | 2.5 ± 0.5 |
| 12. | Allopregnane-3α or 3β,17α,21-triol-11,20-dione | Reichstein D | THE (264) | 2.4 ± 0.5 |
| 13. | Allopregnane-3α or 3β, 11β,17α,21-tetrol-20-one | Reichstein C or Reichstein V | THF (260, 261) | 2.5 ± 0.5 |
| 14. | Allopregnane-3β,17α,20β-21-tetrol | Reichstein K | HHS (250) | 2.0 ± 0.5 |
| 15. | Allopregnane-3β, 11β, 17α, 20β,21-pentol | Reichstein A | HHF (258) | 2.0 ± 0.5 |
| 16. | Deoxycorticosterone | Reichstein Q | DOC (2863) | 3.0 ± 0.5 |
| 17. | 18-Hydroxy-deoxycorticosterone | | 18-OH—DOC (cf 2863) | 1.5 ± 0.3 |
| 18. | Aldosterone | | Ald (219) | 3.0 ± 0.5 |
| | | | | 100.0 |

*Monograph number, The Merck Index, 9th Edition (1976)
**in percent by weight on the dry weight basis of the entire composition In the above table opposite each ingredient the relevant monograph numbers are given from The Merck Index, 9th Edition (1976); the noted monographs being incorporated herein by reference. The reader is referred to Merck Index for a complete chemical, name, source, etc., for each ingredient.

Further in the above table for compounds 6, 7 or 8 an hydroxyl group may be present in the 5-position or both the 5- and 20-position. As for compounds 9 through 13, referring to 3β,21-Dihydroxy-5α-pregame-11,20-dione, which is another chemical name for compound No. 9 (as an example), the configuration may be: 5α,3β; 5α,3α; 5β,3α or 5β,3β for any of compounds 9–13.

The pharmacological rationale of using the compositions of my invention in shock therapy was established by comparison against hydrocortisone base according to the following procedures:

Survival of adrenectomized mice was measured according to Bonskov and Bahnsen (6) B. Bonskov, R. Bahsen, Arch. Exptl. Path. Pharmacol. 178,1 (1935). Lots of adrenectomized mice weighing 10±1 gr each, are observed for survival during a daily treatment with different doses of the adrenosteroid composition given above, and hydrocortisone as a standard, in distilled water against adrenectomized controls treated with distilled water. All the controls died. The survival of 80% of the animals is obtained by a daily administration of about 3 mcg of the adrenosteroids formulation given above, which corresponds to about ⅓ of the dose required of the standard hydrocortisone base.

Alterations of the course of endotoxin shock in dogs, according to R. C. Lillehei et al, Clin. Pharm. Therap. 5,63 (1964) were also studied. Fifteen mg./Kg hydrocortisone or equivalent doses of the adrenosteroid composition given above were intravenously given to lots of mongrel dogs for 1 to 4 days prior to the experiment. Animals are given 1.75 mg/Kg of purified E. coli endotoxin (Difco Labs.). Controls died in about 10 hours. Hematocrit increase, plasma loss, hemoglobin in plasma increase are all evaluated in treated permanent survivors (about 90%). Glycemia and lactic acidemia are also monitored according to the method of J. J. Schuler et al, Ann. Surg. 183,345 (1976).

The invention will now be further illustrated with reference to the following examples in which all parts and percentages are by weight unless otherwise stated.

EXAMPLE 1

The adrenosteroid composition of Table 1 (15 g) containing the different hormones (as bases) are totally dissolved in 1 L of absolute ethanol and then filtered. The ethanol solution is slowly added to 50 L of a 2.5% glucose solution in pyrogen-free water. The solution is vacuum concentrated to 25 liters to make a final concentration of 600 mg/L steroids, 5% glucose and no trace of ethanol. A preservative may be added if desired. The product is then sterile filtered and aseptically filled into 250—or 500 ml sterile plastic bags or glass bottles for infusion.

EXAMPLE 2

The adrenosteroid composition of Table 1 (15 g) is dissolved in 1 L ethanol and slowly added to 50 L pyrogen-free water as in Example 1. The solution is vacuum concentrated to 25 L then 6% Dextran 70 or 10% Dextran 40+5% dextrose is added. Sterile filter and aseptically filled as in Example 1.

What is claimed is:

1. A pharmaceutical composition consisting essentially, in percent by weight, of the following adrenosteroids:

| 1. | 11-Dehydrocorticosterone | 10.0 ± 1.5 |
|---|---|---|
| 2. | Corticosterone | 18.5 ± 2.5 |
| 3. | 11-Deoxy-17-hydroxycorticosterone | 3.0 ± 0.5 |
| 4. | Cortisone | 14.0 ± 2.0 |
| 5. | Hydrocortisone | 23.0 ± 3.5 |
| 6. | 4-Pregnene-5 and/or 20,21-diol or triol-3,11-dione | 2.0 ± 0.5 |
| 7. | 4-Pregnene-5,17α,20β,21-triol or tetrol-3,11-dione | 2.0 ± 0.5 |

| | -continued | |
|---|---|---|
| 8. | 4-Pregnene-5,11β,17α,20β,21-tetrol-3-one | 3.0 ± 0.5 |
| 9. | 3α or β,21-Dihydroxy-5α or β-pregnane-11,20-dione | 2.5 ± 0.5 |
| 10. | 3α or β,11β,21-Trihydroxy-5α or β-pregnan-20-one | 3.0 ± 0.5 |
| 11. | 3α or β,17,21-Trihydroxy-5α or β-pregnan-20-one | 2.5 ± 0.5 |
| 12. | 3α or β,17,21-Trihydroxy-5α or β-pregnane-11,20-dione | 2.4 ± 0.5 |
| 13. | 3α or β,17,21-Tetrahydroxy-20-oxo-5α or β-pregnane | 2.5 ± 0.5 |
| 14. | Allopregnane-3β,17α,20β-21-tetrol | 2.0 ± 0.5 |
| 15. | Allopregnane-3β,11β,17α,20β,21-pentol | 2.0 ± 0.5 |
| 16. | Deoxycorticosterone | 3.0 ± 0.5 |
| 17. | 18-Hydroxy-deoxycorticosterone | 1.5 ± 0.3 |
| 18. | Aldosterone | 3.0 ± 0.5 | together with a pharmaceutically acceptable carrier or diluent.

2. The pharmaceutical composition as claimed in claim 1 in the form of parenteral solution.

3. The pharmaceutical composition as claimed in claim 1 or 2 in the form of sterile, isotonic aqueous solution.

4. The pharmaceutical composition as claimed in claim 1 or 2 in the form of an emulsion.

5. The sterile, isotonic aqueous solution as claimed in claim 3 containing about 0.06 percent by weight of the adrenosteroid composition.

6. The emulsion as claimed in claim 4 containing about 0.06 percent by weight of the adrenosteroid composition.

7. The pharmaceutical composition as claimed in claim 1 also including dextran, dextrose, glucose, plasma, amino acids, lipids or mixtures thereof.

8. A method of treating the effects of shock comprising administering to a mammal suffering therefrom a symptom ameliorating amount of a pharmaceutical composition consisting essentially, in percent by weight of:

| | | |
|---|---|---|
| 1. | 11-Dehydrocorticosterone | 10.0 ± 1.5 |
| 2. | Corticosterone | 18.5 ± 2.5 |
| 3. | 11-Deoxy-17-hydroxycorticosterone | 3.0 ± 0.5 |
| 4. | Cortisone | 14.0 ± 2.0 |
| 5. | Hydrocortisone | 23.0 ± 3.5 |
| 6. | 4-Pregnene-5 and/or 20,21-diol or triol-3,11-dione | 2.0 ± 0.5 |
| 7. | 4-Pregnene-5,17α,20β,21-triol or tetrol-3,11-dione | 2.0 ± 0.5 |
| 8. | 4-Pregnene-5,11β,17α,20β,21-tetrol-3-one | 3.0 ± 0.5 |
| 9. | 3α or β,21-Dihydroxy-5α or β-pregnane-11,20-dione | 2.5 ± 0.5 |
| 10. | 3α or β,11,21-Trihydroxy-5α or β-pregnan-20-one | 3.0 ± 0.5 |
| 11. | 3α or β,17,21-Trihydroxy-5α or β-pregnan-20-one | 2.5 ± 0.5 |
| 12. | 3α or β,17,21-Trihydroxy-5α or β-pregnane-11,20-dione | 2.4 ± 0.5 |
| 13. | 3α or β,17,21-Tetrahydroxy-20-oxo-5α or β-pregnane | 2.5 ± 0.5 |
| 14. | Allopregnane-3β,17α,20β-21-tetrol | 2.0 ± 0.5 |
| 15. | Allopregnane-3β,11β,17α,20β,21-pentol | 2.0 ± 0.5 |
| 16. | Deoxycorticosterone | 3.0 ± 0.5 |
| 17. | 18-Hydroxy-deoxycorticosterone | 1.5 ± 0.3 |
| 18. | Aldosterone | 3.0 ± 0.5 |

9. The method as claimed in claim 8 wherein the shock symptoms being treated are caused by septic shock, traumatic shock or the shock resulting from burns.

10. The method as claimed in claim 8 or 9 wherein the pharmaceutical composition also includes dextran, dextrose, glucose, plasma, amino acids, lipids or mixtures thereof.

11. The method as claimed in claim 8 wherein the pharmaceutical composition is administered parentally to the mammal.

* * * * *